(12) United States Patent
Bathe

(10) Patent No.: US 7,799,916 B2
(45) Date of Patent: Sep. 21, 2010

(54) PROCESS FOR THE PREPARATION OF 5-(4-[4-(5-CYANO-3-INDOLYL)BUTYL]-1-PIPERAZINYL)BENZOFURAN-2-CARBOXAMIDE

(75) Inventor: Andreas Bathe, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 261 days.

(21) Appl. No.: 11/912,584

(22) PCT Filed: Apr. 12, 2006

(86) PCT No.: PCT/EP2006/003344

§ 371 (c)(1), (2), (4) Date: Jun. 24, 2008

(87) PCT Pub. No.: WO2006/114202

PCT Pub. Date: Nov. 2, 2006

(65) Prior Publication Data

US 2008/0293943 A1 Nov. 27, 2008

(30) Foreign Application Priority Data

Apr. 26, 2005 (DE) .................. 10 2005 019 670

(51) Int. Cl.
*C07D 405/12* (2006.01)
(52) U.S. Cl. .................. 544/373; 514/254.09
(58) Field of Classification Search .................. None
See application file for complete search history.

(56) References Cited

U.S. PATENT DOCUMENTS 5,532,241 A * 7/1996 Bottcher et al. ........ 514/254.09
7,572,796 B2 * 8/2009 Schadt et al. .......... 514/254.09

OTHER PUBLICATIONS

Heinrich et al. J. Med. Chem. vol. 47 (19), p. 4677-4683 (2004).*
Heinrich et al., Synthessi and Structure-Activity Relationship in a Class of Indolebutylpiperazines as Dual 5-HT 1A Receptor Agonists and Serotonin Reuptake Inhibitors, Journal of Medicinal Chemistry, Bd. 47, Nr. 19, pp. 4684-4692, (2004).

* cited by examiner

*Primary Examiner*—Emily Bernhardt
(74) *Attorney, Agent, or Firm*—Millen, White, Zelano & Branigan, P.C.

(57) ABSTRACT

The invention relates to a process for the preparation of 5-(4-[4-(5-cyano-3-indolyl)butyl]-1-piperazinyl)benzofuran-2-carboxamide and/or one of its physiologically acceptable salts, characterized in that a compound of the formula (I), in which L denotes Cl, Br, I, $SO_2F$, $SO_2CF_3$, $SO_2C_2F_5$, is reacted with 3-(4-piperazin-1-ylbuyl)indole-5-carbonitrile by transition-metal-catalyzed coupling by means of Pd complexes, and/or in that the 5-(4[4-(5-cyano-3-indolyl)butyl]-1-piperazinyl)benzofuran-2-carboxamide formed is converted into one of its acid-addition salts by treatment with an acid, and to a second process, characterized in that a compound of the formula (II), as the base or HX salt (where X=Cl, BR), is reacted with 3-(4-oxobutyl)-1H-indole-5-carbonitrile by reductive amination, and/or in that 5-(4-[4-(5-cyano-3-indolyl)butyl]-1-piperazinyl)benzofuran-2-carboxamide is converted into one of its acid-addition salts by treatment with an acid.

(I)

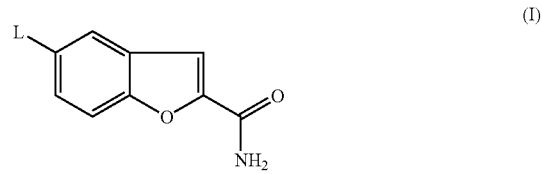

4 Claims, No Drawings

PROCESS FOR THE PREPARATION OF 5-(4-[4-(5-CYANO-3-INDOLYL)BUTYL]-1-PIPERAZINYL)BENZOFURAN-2-CARBOXAMIDE

The invention relates to a process for the preparation of 5-(4-[4-(5-cyano-3-indolyl)butyl]-1-piperazinyl)benzofuran-2-carboxamide and physiologically acceptable salts thereof by chemoselective, metal-catalysed coupling of the precursor 3-(4-piperazin-1-ylbutyl)indole-5-carbonitrile to halogenated benzofuran-2-carboxamide derivatives.

The invention furthermore relates to a process for the preparation of 5-(4-[4-(5-cyano-3-indolyl)butyl]-1-piperazinyl)benzofuran-2-carboxamide and physiologically acceptable salts thereof by reductive amination of 3-(4-oxobutyl)-1H-indole-5-carbonitrile using 5-piperazinylbenzofuran-2-carboxamide.

The access to date is based on the coupling of an activated 5-cyano-3-butylindole to 5-piperazinylbenzofuran derivatives, as known, for example, from J. Med. Chem. (2004), 47(19), 4684-4692, Heinrich, T.; Boettcher, H.; Gericke, R.; Bartoszyk, G. D.; Anzali, S.; Seyfried, C. A.; Greiner, H. E.; van Amsterdam, C. and J. Med. Chem. 2004, 47, 4677-4683, Heinrich, T, Böttcher, H. Bartoszyk, G. D. Greiner, H. E. Seyfried, C. A., van Amsterdam, C. and literature cited therein.

Surprisingly, investigations as part of the synthesis of medicaments, which are described, for example, in EP 0 648 767, have now shown that 5-(4-[4-(5-cyano-3-indolyl)butyl]-1-piperazinyl)benzofuran-2-carboxamide can be obtained in at least comparable or higher overall yield compared with the prior art, where crucial advantages which may be mentioned here are the simple reaction comprising fewer synthetic steps and consequently simple product isolation.

This consequently also means lower solvent and energy consumption.

The invention thus relates to a process for the preparation of 5-(4-[4-(5-cyano-3-indolyl)butyl]-1-piperazinyl)benzofuran-2-carboxamide and/or one of its physiologically acceptable salts, where a compound of the formula I

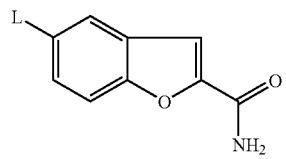

I in which
L denotes Cl, Br, I, $SO_2F$, $SO_2CF_3$, $SO_2C_2F_5$,
is reacted with 3-(4-piperazin-1-ylbutyl)indole-5-carbonitrile by transition-metal-catalysed coupling by means of Pd complexes,
and/or in that the 5-(4-[4-(5-cyano-3-indolyl)butyl]-1-piperazinyl)benzofuran-2-carboxamide formed is converted into one of its acid-addition salts by treatment with an acid. (Process variant a))

The radical L used is preferably bromine.

The above-mentioned process variant a) is thus based on metal-catalysed coupling of a piperazine to a 5-haloindole derivative, preferably a 5-bromoindole derivative, in the presence of a transition-metal catalyst and leads to the above-mentioned end product. Compared with the processes known from the prior art, which can comprise up to 10 steps, this process variant is significantly shorter and thus also less expensive.

The transition-metal catalysts employed are preferably Pd(0) complexes, such as tris(dibenzylideneacetone)dipalladium or analogous complexes in combination with phosphorus ligands, such as, for example, $P(t-Bu)_3$. However, $Pd^{2+}$ derivatives, such as, for example, $PdCl_2$ or $Pd(OAc)_2$, can also be used as palladium source.

Processes for the preparation of 5-(1-piperazinyl)benzofuran-2-carboxamide are known, for example, from WO 01/40219 (Merck Patent GmbH), where a transition-metal catalyst is used. For the metal-catalytic coupling, aprotic solvents, such as toluene, xylene, THF or other ethers, are used.

Suitable bases are alkali metal alkoxides, preferably sodium tert-butoxide, or also alkali metal carbonates.

Depending on the reaction conditions used, the reaction time is between a few minutes and 7 days, the reaction temperature is between 0 and 150° C., preferably between 20° and 120° C.

The invention also relates to a process for the preparation of 5-(4-[4-(5-cyano-3-indolyl)butyl]-1-piperazinyl)benzofuran-2-carboxamide and/or one of its physiologically acceptable salts, where a compound of the formula II

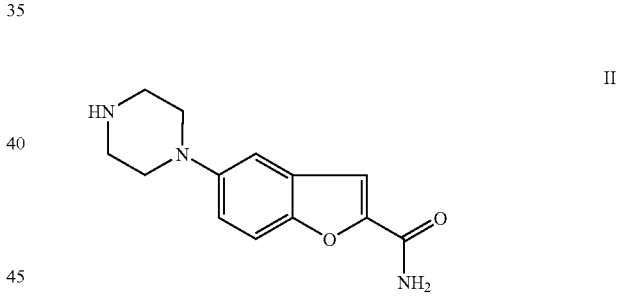

II as the base or HX salt (where X=Cl, Br, sulfate or also organic counterions, such as, for example, the methanesulfonic acid anion ($CH_3$ $SO_3^-$)), is reacted with 3-(4-oxobutyl)-1H-indole-5-carbonitrile by reductive amination, and/or where the 5-(4-[4-(5-cyano-3-indolyl)butyl]-1-piperazinyl)benzofuran-2-carboxamide formed here is converted into one of its acid-addition salts by treatment with an acid (process variant b)).

The reductive amination (process variant b)) of aldehydes is a widespread amine synthesis (see Baxter, E. W.; Reitz, A. B. Organic Reactions 2002, 59, 1). In the present process, firstly the aldehyde 3-(4-oxobutyl)-1H-indole-5-carbonitrile is obtained from 3-(4-hydroxybutyl)-1H-indole-5-carbonitrile. The aldehyde is coupled to a compound of the formula II in the subsequent step with addition of reducing agents, where 5-(4-[4-(5-cyano-3-indolyl)butyl]-1-piperazinyl)benzofuran-2-carboxamide is formed as the base and can be isolated using conventional laboratory methods or alternatively the base is converted into the monohydrochloride (vilazodone) in solution or as the solid after treatment with acids, such as, for example, hydrochloric acid. Replacement of the alkylation step with reagent 3-(4-chlorobutyl)indole-5-carbonitrile, as described in J. Med. Chem. (2004), 47(19), 4684-4692, Heinrich, T.; Boettcher, H.; Gericke, R.; Bartoszyk, G. D.; Anzali, S.; Seyfried, C. A.; Greiner, H. E.; van Amsterdam, C. and literature cited therein, by a reductive amination using (3-(4-oxobutyl)-1H-indole-5-carbonitrile) is thus possible.

Suitable solvents are alcohols, preferably methanol, but also ethers, hydrocarbons or other solvents which dissolve the starting materials to an adequate extent. Depending on the reaction conditions used, the reaction time is between a few minutes and 7 days, the reaction temperature is between 0 and 150° C., preferably between 0° and 30° C.

In the following examples, "conventional laboratory workup" means this procedure: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

The base of 5-(4-[4-(5-cyano-3-indolyl)butyl]-1-piperazinyl)benzofuran-2-carboxamide can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as HCl or HBr, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, Metal-Catalytic Amination (Process Variant a))

EXAMPLE 1

Under protective gas, 80 mg of tris(dibenzylideneacetone) dipalladium and 65 mg of tris-tert-butylphosphine are introduced into 70 ml of diethylene glycol dimethyl ether at 20° C. with stirring. 1.5 g of 5-bromobenzofuran-2-carboxamide and 2.5 g of 3-(4-piperazin-1-ylbutyl)indole-5-carbonitrile are subsequently introduced. On subsequent addition of 2.3 g of sodium tert-butoxide, a yellow-grey suspension forms. The reaction mixture is heated at 120° C. for 48 hrs, then the reaction mixture is cooled to RT (about 23° C.), worked up using conventional laboratory methods, and the target compound is isolated, optionally as the base of vilazodone or as the monohydrochloride (=vilazodone/5-{4-[4-(5-cyano-3-indolyl)butyl]-1-piperazinyl}benzofuran-2-carboxamide hydrochloride) after treatment of the dissolved base with aqueous hydrochloric acid.

The identity of the target compound was confirmed by chromatographic comparison with reference material.

Reductive Amination (Process Variant b))

EXAMPLE 2

Precursor 3-(4-oxobutyl)-1H-indole-5-carbonitrile 18 g of 3-(4-hydroxybutyl)-1H-indole-5-carbonitrile and 34 ml of triethylamine are dissolved in 300 ml of dichloromethane and cooled to about 0° C. in an ice/methanol bath. A solution of 39 g of sulfur trioxide/pyridine complex and 140 ml of dimethyl sulfoxide is subsequently metered in at 2 to 5° C. The mixture is stirred at 2 to 3° C. for approximately a further 20 min., then the reaction solution is warmed to 22-23° C. (room temperature) over the course of 2 hrs. The reaction mixture is diluted by addition of a further 200 ml of dichloromethane and then extracted with water, 10% citric acid solution and 10% sodium chloride solution. The organic phase is concentrated to an oily residue in vacuo, then chromatographed on silica gel using a mixture of dichloromethane and MTB ether.

A comparative H-NMR and MS confirm the identity.

Preparation of 5-{4-[4-(5-cyano-3-indolyl)butyl]-1-piperazinyl}benzofuran-2-carboxamide hydrochloride At 20° C. 1.7 g of 5-(1-piperazinyl)benzofuran-2-carboxamide and 1.1 g of sodium cyanoborohydride are dissolved in 200 ml of methanol with stirring. A solution of 2.4 g of 3-(4-oxobutyl)-1H-indole-5-carbonitrile and 50 ml of methanol are added over the course of 15 min. at this temperature. The reaction mixture is stirred at 20° C. for approx. 18 h, then cooled to 10° C. for 6 hrs. The precipitated solid product is separated off, washed with methanol and water and dried in vacuo. The solid remaining is dissolved tetrahydrofuran at 20° C. with stirring and filtered. Aqueous 1 N HCl is added to the filtrate. The reaction mixture is stirred further at 20° C., then the precipitated solid product is filtered off. The filter residue is washed with THF and water and dried thermally in vacuo.

According to chromatographic comparison with reference material, the solid obtained is the target compound vilazodone (5-{4-[4-(5-cyano-3-indolyl)butyl]-1-piperazinyl}benzofuran-2-carboxamide hydrochloride).

The invention claimed is:

1. A process for the preparation of 5-(4-[4-(5-cyano-3-indolyl)butyl]-1-piperazinyl)benzofuran-2-carboxamide and/or a physiologically acceptable salt thereof, comprising reacting a compound of the formula I

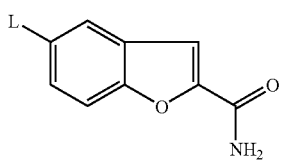

in which

L is Cl, Br, I, SO$_2$F, SO$_2$CF$_3$ or SO$_2$C$_2$F$_5$, with 3-(4-piperazin-1-ylbutyl)indole-5-carbonitrile by transition-metal-catalysed coupling by means of a Pd complex, and/or converting the 5-(4-[4-(5-cyano-3-indolyl)butyl]-1-piperazinyl)benzofuran-2-carboxamide formed into an acid addition salt thereof by treatment with an acid.

2. A process according to claim 1, wherein L is Br.

3. A process according to claim 1, wherein the transition-metal catalyst system used is tris(dibenzylideneacetone)-dipalladium or an analogous Pd(0) complexe.

4. A process for the preparation of 5-(4-[4-(5-cyano-3-indolyl)butyl]-1-piperazinyl)benzofuran-2-carboxamide and/or a physiologically acceptable salt thereof, comprising reacting a compound of the formula II

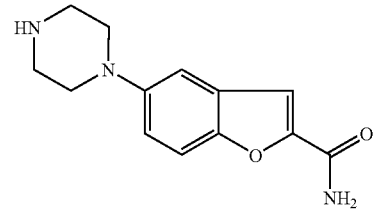

II as the base or HX salt (where X=Cl, Br), with 3-(4-oxobutyl)-1H-indole-5-carbonitrile by reductive amination, and/or converting 5-(4-[4-(5-cyano-3-indolyl)butyl]-1-piperazinyl)benzofuran-2-carboxamide into an acid addition salt thereof by treatment with an acid.

* * * * *